US011622675B2

(12) United States Patent
Powell et al.

(10) Patent No.: US 11,622,675 B2
(45) Date of Patent: Apr. 11, 2023

(54) MEDICAL DEVICE HAVING ASYMMETRIC BENDING

(71) Applicant: Boston Scientific Scimed, Inc., Maple Grove, MN (US)

(72) Inventors: Sean Powell, Holden, MA (US); Almir Velagic, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 185 days.

(21) Appl. No.: 15/930,807

(22) Filed: May 13, 2020

(65) Prior Publication Data

US 2020/0359873 A1 Nov. 19, 2020

Related U.S. Application Data

(60) Provisional application No. 62/848,195, filed on May 15, 2019.

(51) Int. Cl.
*A61B 1/008* (2006.01)
*A61B 1/005* (2006.01)

(52) U.S. Cl.
CPC ............ *A61B 1/008* (2013.01); *A61B 1/0052* (2013.01)

(58) Field of Classification Search
CPC ...... A61B 1/008; A61B 1/0052; A61B 1/0056
See application file for complete search history.

(56) References Cited

U.S. PATENT DOCUMENTS

| 4,279,245 A | 7/1981 | Takagi et al. |
| 4,580,551 A | 4/1986 | Siegmund et al. |
| 4,911,148 A | 3/1990 | Sosnowski et al. |
| 5,235,964 A | 8/1993 | Abenaim |
| 6,364,828 B1 | 4/2002 | Yueng et al. |
| 6,491,626 B1 | 12/2002 | Stone et al. |
| 6,749,560 B1 | 6/2004 | Konstorum et al. |
| RE40,475 E | 9/2008 | Hornsbostel et al. |
| 7,678,117 B2 | 3/2010 | Hinman et al. |
| 7,785,252 B2 | 8/2010 | Danitz et al. |

(Continued)

FOREIGN PATENT DOCUMENTS

| EP | 1 819 266 B1 | 8/2007 |
| EP | 2 124 800 B1 | 12/2009 |
| EP | 3 195 784 A1 | 7/2017 |

*Primary Examiner* — Alexandra L Newton
*Assistant Examiner* — Rynae E Boler
(74) *Attorney, Agent, or Firm* — Bookoff McAndrews, PLLC

(57) ABSTRACT

An articulation joint includes proximal links, distal links, and intermediate links connecting the proximal and distal links. The articulation joint has a straight configuration along a straight longitudinal axis, a first bent configuration when the articulation joint bends toward a first side of the longitudinal axis, and a second bent configuration when the articulation joint bends toward a second side of the longitudinal axis, opposite to the first side. When the articulation joint is in the straight configuration, a first gap is defined at the first side between adjacent proximal links, and the adjacent proximal links contact each other at the second side, a second gap is defined at each of the first side and the second side between adjacent distal links, and a third gap is defined at the first side between adjacent intermediate links, and adjacent intermediate links contact each other at the second side.

20 Claims, 4 Drawing Sheets

(56) References Cited

U.S. PATENT DOCUMENTS

| | | | |
|---|---|---|---|
| 7,862,580 B2 | 1/2011 | Cooper et al. |
| 8,052,597 B2 | 11/2011 | Boulais |
| 8,206,286 B2 | 6/2012 | Sato |
| 8,323,297 B2 | 12/2012 | Hinman et al. |
| 8,428,710 B2 | 4/2013 | Kuriyama et al. |
| 8,460,213 B2 | 6/2013 | Northrop |
| 8,580,063 B2 | 11/2013 | Koori et al. |
| 8,622,894 B2 | 1/2014 | Banik et al. |
| 8,663,090 B2 | 3/2014 | Fujimoto |
| 8,734,695 B2 | 5/2014 | Yago et al. |
| 8,790,243 B2 | 7/2014 | Cooper et al. |
| 8,795,254 B2 | 8/2014 | Layman et al. |
| 8,821,477 B2 | 9/2014 | Northrop et al. |
| 8,979,739 B2 | 3/2015 | Seto et al. |
| 8,992,422 B2 | 3/2015 | Spivey et al. |
| 9,095,253 B2 | 8/2015 | Hinman et al. |
| 9,138,131 B2 | 9/2015 | Sato |
| 9,227,037 B2 | 1/2016 | Northrop |
| 9,439,557 B2 | 9/2016 | Boulais |
| 9,462,932 B2 | 10/2016 | Ostrovsky et al. |
| 9,585,546 B2 | 3/2017 | Surti et al. |
| 9,737,200 B2 | 8/2017 | Makiyama |
| 9,820,635 B2 | 11/2017 | Seto et al. |
| 9,861,786 B2 | 1/2018 | Hinman et al. |
| 10,052,013 B2 | 8/2018 | Boulais |
| 10,172,670 B2 | 1/2019 | Stewart et al. |
| 10,292,575 B2 | 5/2019 | Surti et al. |
| 10,321,804 B2 | 6/2019 | Jacobsen et al. |
| 10,328,241 B2 | 6/2019 | Verbeek |
| 10,478,045 B2 | 11/2019 | Nagai et al. |
| 10,524,868 B2 | 1/2020 | Cooper et al. |
| 2004/0199052 A1 | 10/2004 | Banak et al. |
| 2004/0225186 A1 | 11/2004 | Horne, Jr. et al. |
| 2005/0015072 A1 | 1/2005 | Engel et al. |
| 2005/0182298 A1 | 8/2005 | Ikeda et al. |
| 2006/0106288 A1* | 5/2006 | Roth ................ A61B 17/072 |
| | | | 604/206 |
| 2008/0026561 A1 | 1/2008 | Hsu et al. |
| 2008/0059861 A1 | 3/2008 | Zhang |
| 2009/0177040 A1 | 7/2009 | Lyons et al. |
| 2009/0318764 A1 | 12/2009 | Yoshimoto et al. |
| 2010/0130823 A1 | 5/2010 | Ando |
| 2010/0201029 A1 | 8/2010 | Yago et al. |
| 2010/0312056 A1 | 12/2010 | Galperin et al. |
| 2011/0112365 A1 | 5/2011 | Galperin et al. |
| 2011/0230718 A1 | 9/2011 | Akui |
| 2011/0306831 A1 | 12/2011 | Kohnke et al. |
| 2013/0261396 A1 | 10/2013 | Boulais et al. |
| 2014/0142377 A1* | 5/2014 | Yang ................ A61B 34/30 |
| | | | 600/104 |
| 2014/0336620 A1 | 11/2014 | Layman et al. |
| 2015/0202352 A1 | 7/2015 | Watanabe et al. |
| 2016/0024343 A1 | 1/2016 | Nakai et al. |
| 2016/0310701 A1* | 10/2016 | Pai ................ A61B 1/0055 |
| 2016/0317185 A1 | 11/2016 | Krieger et al. |
| 2017/0000795 A1 | 1/2017 | Cade et al. |
| 2017/0007803 A1 | 1/2017 | Ostrovsky et al. |
| 2017/0086652 A1 | 3/2017 | Nakade et al. |
| 2017/0095138 A1 | 4/2017 | Nakade et al. |
| 2017/0172385 A1 | 6/2017 | Fujitani et al. |
| 2017/0224192 A1 | 8/2017 | Seto et al. |
| 2017/0224194 A1 | 8/2017 | Fujitani et al. |
| 2018/0104448 A1 | 4/2018 | Hinman et al. |
| 2018/0168432 A1 | 6/2018 | Banik et al. |
| 2018/0289242 A1 | 10/2018 | Dai |
| 2018/0325357 A1 | 11/2018 | Boulais |
| 2019/0059699 A1 | 4/2019 | Ting |

* cited by examiner

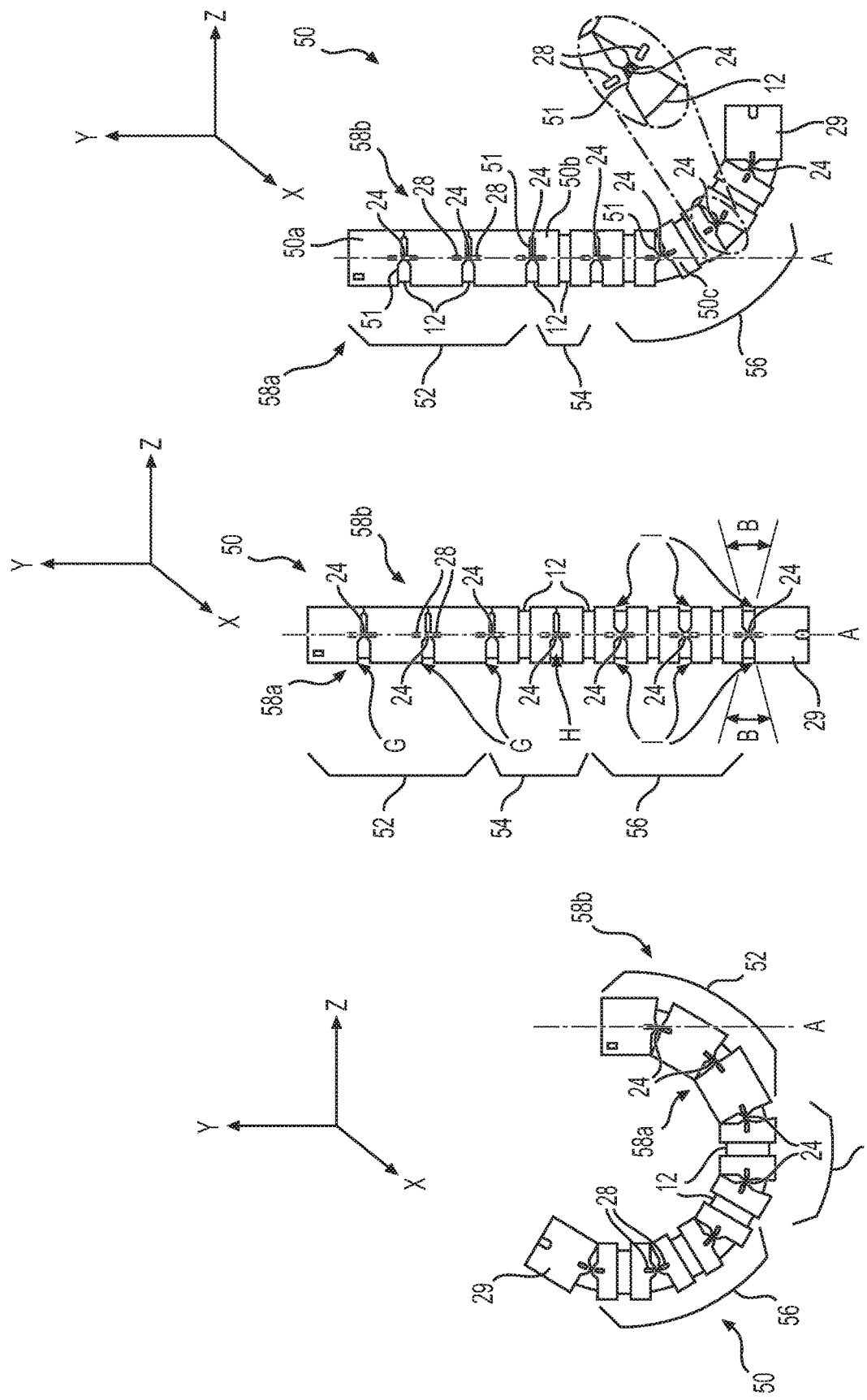

MEDICAL DEVICE HAVING ASYMMETRIC BENDING

CROSS-REFERENCE TO RELATED APPLICATIONS

This application claims the benefit of priority from U.S. Provisional Application No. 62/848,195, filed May 15, 2019, which is incorporated by reference herein in its entirety.

TECHNICAL FIELD

The present disclosure relates generally to endoscopic medical devices and methods of use. More particularly, in some embodiments, the disclosure relates to endoscopes and methods related for accessing target sites having space constraints, using, e.g., a flexible steerable shaft such as an articulation joint at a distal end of the endoscope.

BACKGROUND

Endoscope devices generally include a flexible shaft, a working distal tip, and a flexible steerable shaft joining the working tip and the flexible shaft. The flexible steerable shaft may include a bendable articulation joint. Drawbacks of conventional endoscopes include, for example, the inability to provide a small bend radius when the articulation joint provides both large and small bend angles. For example, articulation joints providing full retroflex (bending of the articulation joint to visualize proximally, for example an entry portal of the endoscope into a patient's stomach) generally require the articulation joint to bend by approximately 210 degrees or more. When the same conventional articulation joint is bent to less than 210 degrees, e.g., a 90 degree position, the articulation joint will make a gradual turn with a large radius, which is not suitable for areas of the human body having space constraints. These drawbacks can prevent the physician from properly visualizing and/or accessing areas of the body during procedures.

Accordingly, it is desirable for the articulation joint to provide a tightest acceptable bend radius when flexing the articulation joint to a maximum angle, and to achieve the same or similar tightest acceptable bend radius when flexing the articulation joint to a smaller angle. The present disclosure may solve one or more of these problems or other problems in the art. The scope of the disclosure, however, is defined by the attached claims and not the ability to solve a specific problem.

SUMMARY OF THE DISCLOSURE

According to an example, an articulation joint for a medical device includes proximal links, distal links, and intermediate links connecting the proximal and distal links. The articulation joint has a straight configuration along a straight longitudinal axis, a first bent configuration when the articulation joint bends toward a first side of the longitudinal axis, and a second bent configuration when the articulation joint bends toward a second side of the longitudinal axis, opposite to the first side. When the articulation joint is in the straight configuration, a first gap is defined at the first side between adjacent proximal links, and the adjacent proximal links contact each other at the second side, a second gap is defined at each of the first side and the second side between adjacent distal links, and a third gap is defined at the first side between adjacent intermediate links, and adjacent intermediate links contact each other at the second side.

When the articulation joint is in the first bent configuration, a size of each of the first, second, and third gaps on the first side, may be smaller than a size of the first, second, and third gaps on the first side respectively when the articulation joint is in the straight configuration.

When the articulation joint is completely bent toward the first side, surfaces of adjacent links may contact each other such that the side of each of the first, second, and third gaps on the first side is zero.

When the articulation joint is in the second bent configuration, a size of the second gaps on the second side may be smaller than a size of the second gaps on the second side when the articulation joint is in the straight configuration.

The distal links may be movable in exactly four directions, the proximal links may be movable in exactly one direction, and the intermediate links may be movable in two or three directions.

The articulation joint may include a third bent configuration toward a third side of the longitudinal axis, intermediate to the first and second sides, and a fourth bent configuration when the articulation joint bends toward a fourth side of the longitudinal axis, opposite to the third side, such that when the articulation joint is in the straight configuration, a fourth gap may be defined at each of the third side and the fourth side between the adjacent distal links, and a fifth gap may be defined at each of the third side and the fourth side between the adjacent intermediate links.

When the articulation joint is in the third bent configuration, a size of each of the fourth gaps and the fifth gaps on the third side may be smaller than a size of the fourth gaps and the fifth gaps on the third side respectively when the articulation joint is in the straight configuration, and when the articulation joint is in the fourth bent configuration, a size of each of the fourth gaps and the fifth gaps on the fourth side may be smaller than a size of the fourth gaps and the fifth gaps on the fourth side respectively when the articulation joint is in the straight configuration.

The fourth gaps and the fifth gaps may be offset from the first, second, and third gaps along the longitudinal axis.

The articulation joint may move in one of the first or the second direction and one of the third or the fourth direction at a same time.

Proximal links, distal links, and intermediate links of the articulation joint may be each attached to an adjacent link by a first spring and a second spring, and the first spring and the second spring of attached links may be on circumferentially opposite sides of the articulation joint.

The first and the second springs may be attached on an inner surface of each of the proximal links, distal links, and intermediate links by one or more of welding, brazing, soldering, or an adhesive.

Adjacent coils of each of the first spring and the second spring may contact each other when the first springs and the second springs are in a straight configuration.

Each of the first spring and the second spring may define a lumen for containing an articulation element.

A bend angle associated with each of the first, second, third, fourth, and fifth gaps may be equal.

The articulation joint may include a tip portion attached to a distal end of the distal links, wherein the tip portion includes one or more of an imaging device, lighting device, an end effector, and a cannulation for passage of secondary instrumentation.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 4A-4F are side views of the articulation joint of FIG. 3.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
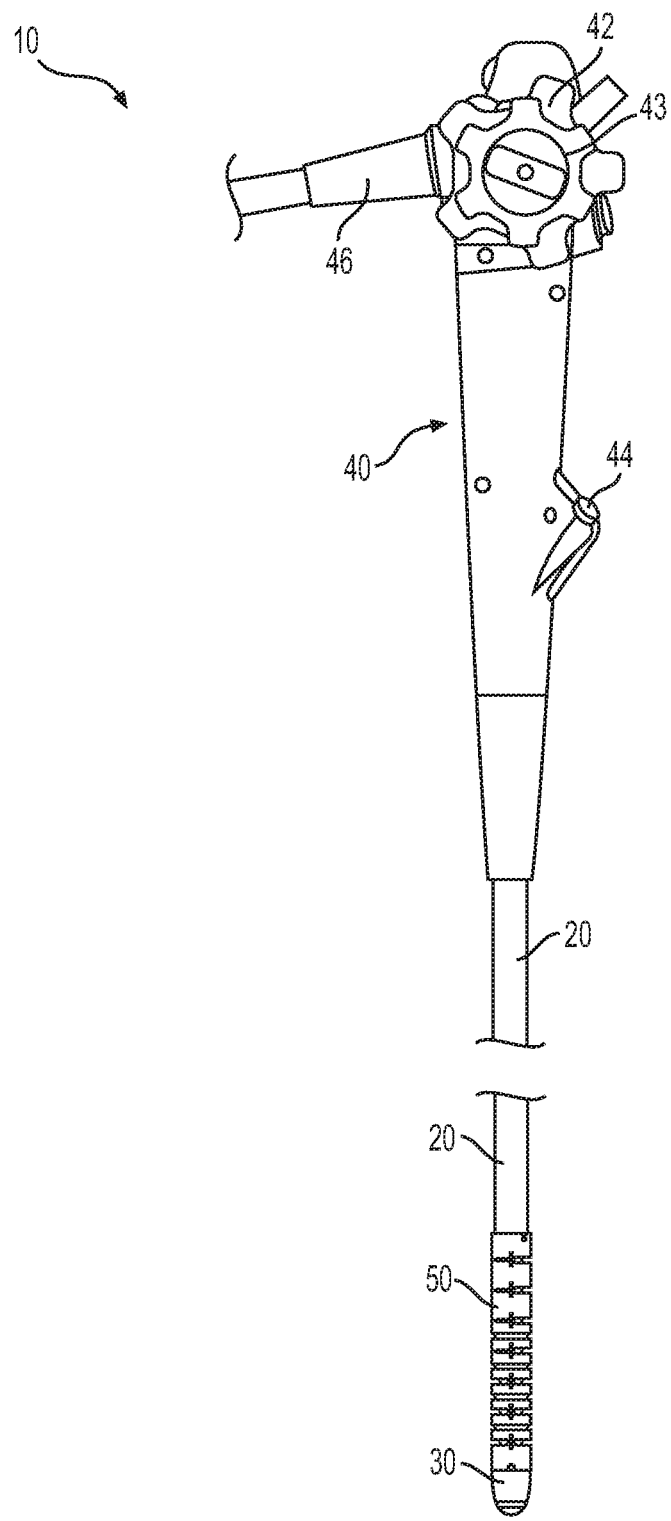
FIG. 1 is a perspective view of a medical device according to an embodiment.

Referring to FIG. 1, an endoscope 10 according to an embodiment is shown. Endoscope 10 includes a flexible shaft 20, a tip 30 at a distal end of endoscope 10, and an articulation joint 50 disposed between and connecting flexible shaft 20 and tip 30. A handle 40 or some other device for actuating or controlling endoscope 10, and any tool or devices associated with endoscope 10, is connected at a proximal end of flexible shaft 20.

A plurality of actuating elements 12, such as cables or wires suitable for medical procedures (e.g., medical grade plastic or metal), extend distally from a proximal end of endoscope 10. Actuating elements 12 are shown between adjacent links in, e.g., FIGS. 4A-4F. Actuating elements 12 may extend into handle 40 and may be indirectly coupled to first and second actuating devices 42, 43, which control articulation of articulation joint 50 in multiple directions. Devices 42, 43, may be, for example, rotatable knobs that rotate about their axes to push/pull actuating elements 12. Alternatively, or additionally, a user may operate actuating elements 12 independently of handle 40. Distal ends of actuating elements 12 extend through flexible shaft 20 and terminate at actuating joint 50 and/or tip 30. For example, one or more actuating elements 12 may be connected to articulation joint 50 and one or more other actuating elements 12 may be attached to tip 30. As will be explained herein, actuation of actuating elements 12 may control actuating joint 50, tip 30, and/or elements attached to tip 30, such as an end effector (not shown). In addition, one or more electrical cables (not shown) may extend from the proximal end of endoscope 10 to tip 30 and may provide electrical controls to imaging, lighting, and/or other electrical devices on tip 30, and may carry imaging signals from tip 30 proximally to be processed and/or displayed on a display. Handle 40 may also include ports 44, 46 for introducing and/or removing tools, fluids, or other materials from the patient. Port 44 may be used to introduce tools. Port 46 may be connected to an umbilicus for introducing fluid suction, and/or wiring for electronic components.

Figure 2:
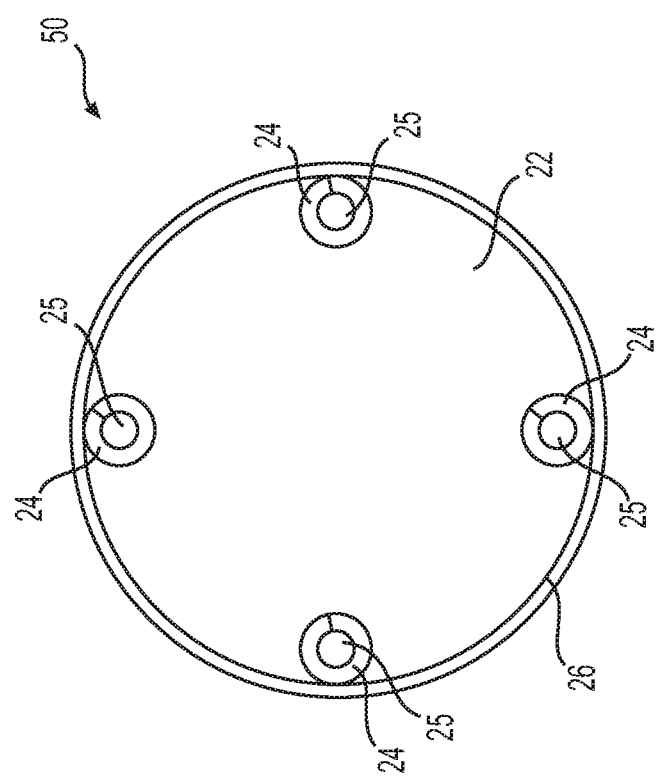
FIG. 2 is a cross-section of an articulation joint of the medical device according to FIG. 3 along the line A-A.

As shown in FIG. 2, articulation joint 50 includes a portion of a lumen 22 that extends through endoscope 10. Articulation joint 50 also includes a plurality of springs 24. For ease of understanding, only some of the plurality of springs 24 are identified in FIG. 3. Further, springs 24 have been removed in FIGS. 4A-4F for ease of understanding (springs 24 are located between pairs of laser welds 28, described below). Springs 24 connect adjacent links of articulation joint 50, as will be described in greater detail herein. Lumen 22 may extend from handle 40 through flexible shaft 20 into articulation joint 50, and through a distal end of tip 30. Lumen 22 may receive tools, imaging devices, and other devices associated with endoscope 10 to perform endoscopic procedures. Further, tissue samples and/or other material may be removed from a patient through lumen 22. It will be understood that endoscope 10, including flexible shaft 20 and articulation joint 50, are not limited to a single lumen 22, and may include any number of lumens necessary for performing procedures. Alternatively, or additionally, one or more catheters (not show) may be introduced through lumen 22 to remove tissue and/or insert tools.

With continued reference to FIG. 2, springs 24 define actuation holes 25 which receive actuation elements 12. According to an example, one actuating element or a plurality of actuating elements 12 may be disposed in a single actuation hole 25 of each spring 24. Additional actuation holes, such as eyelets (not shown), may extend from a proximal end of flexible shaft 20 to a distal end thereof, and may provide a path through which actuation elements 12 may extend, thereby preventing actuating elements 12 from becoming tangled or otherwise adversely affecting an operation of endoscope 10.

Figure 3:
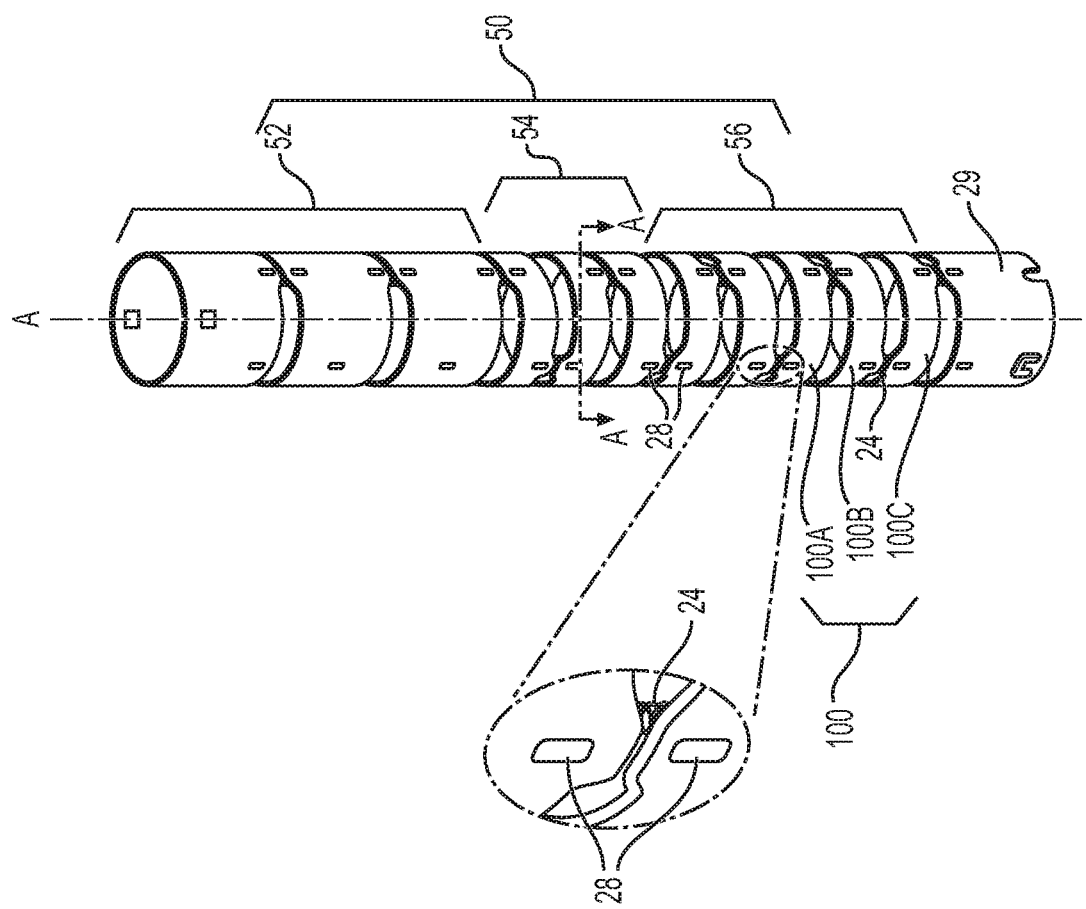
FIG. 3 is a perspective view of the articulation joint of FIG. 2.

With reference to FIG. 3, a distalmost link 29 may connect to tip 30. Tip 30 may include a camera (not shown), lighting, electronics (such as a printed circuit board), an end effector or tool (not shown), or any other device used in a therapeutic or a diagnostic procedure. It will be understood that tip 30 may include multiple elements, e.g., both the camera and the end effector, to both visualize a target site and to collect samples from the target site.

Articulation joint 50 will be described with reference to FIGS. 3 and 4A-4F. Articulation joint 50 includes a plurality of generally cylindrical links with a plurality of gaps provided therebetween. For example, as shown in FIG. 3, articulation joint 50 includes a first proximal link section 52, a third distal link section 56, and a second intermediate link section 54 provided between and connecting the first link section 52 and the third link section 56. First, second, and third link sections 52, 54, 56 are formed of a first link type 50$a$, a second link type 50$b$, and a third link type 50$c$, respectively (see FIG. 4C). According to an example, first, second, and third link types 50$a$, 50$b$, 50$c$ may be the same or different shapes and/or sizes. For example, first link type 50$a$ is longer along longitudinal axis A than second and third link types 50$b$, 50$c$. Unless specified otherwise, first link type 50$a$, second link type 50$b$, and third link type 50$c$ will generally be referred to as a "link." Links may be formed by, for example, laser cutting a tube (such as a metal tube, a plastic tube, or any other medical grade material known in the art), but are not limited to being formed in this manner.

As further shown in FIGS. 2 and 3, springs 24 join adjacent links in each of first, second, and third link sections 52, 54, 56. Additionally, springs 24 may connect a distalmost link of first link section 52 to a proximalmost link of second link section 54, may connect a distalmost link of second link section 54 to a proximalmost link of third link section 56, and/or may connect a distalmost link of third link section 56 to distalmost link 29. As will be described in greater detail herein, adjacent links are capable of bending with respect to each other due to spacing between links and via the flexibility of springs 24. While examples illustrate two springs 24 joining adjacent links, the invention is not limited to this configuration. According to an example, springs 24 are attached to an inner surface of articulation joint 50 by, e.g., laser welding, adhesives, rivets, or any other technique known in the art. For example, laser welds 28 are shown on adjacent links in FIG. 3 at locations at which springs 24 are attached.

Figure 4F:
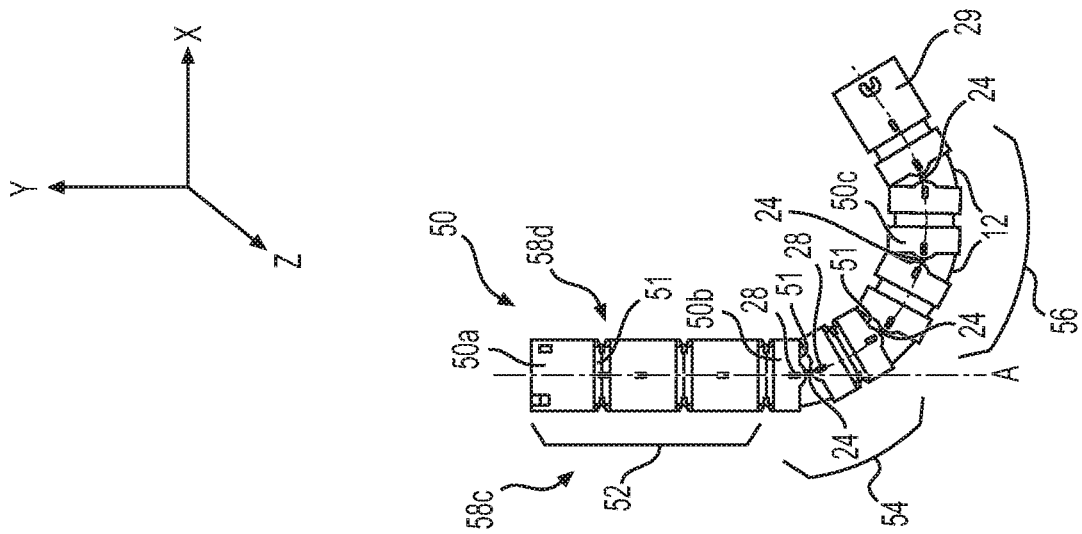
Figure 4E:
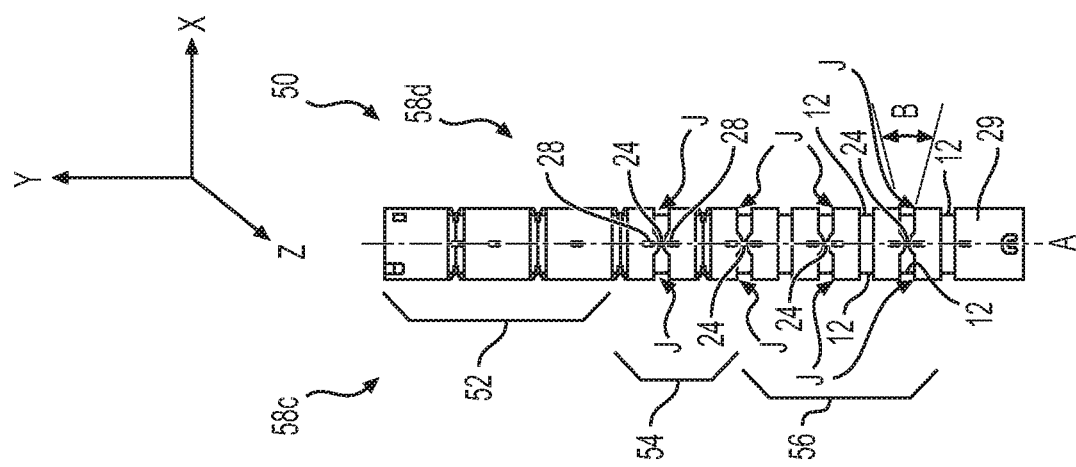

As shown in FIGS. 4B and 4E, articulation joint 50 is in a straight configuration and includes a longitudinal axis A extending through a center of each of first, second, and third link sections 52, 54, 56. Articulation joint 50 is configured to bend in four different directions 90 degrees apart from each other about axis A (e.g., up, down, left and right directions). The directions of bending are designated as first side 58a, second side 58b, third side 58c, and fourth side 58d, approximately 90 degrees from each adjacent side. First side 58a is opposite second side 58b (approximately 180 degrees apart), and third side 58c is opposite fourth side 58d (approximately 180 degrees apart). As shown in FIGS. 4A, 4C, 4D, and 4F, links are bent in each of first, second, and/or third link sections 52, 54, 56 with respect to each other. As further shown in FIGS. 4A-4F, springs 24 are located on only two adjacent sides, e.g., third side 58c and fourth side 58d, of first link section 52. As will be described in greater detail below, springs 24 are located on first, second, third, and fourth sides 58a, 58b, 58c, 58d of second link section 54 and third link section 56.

As shown in FIGS. 4C and 4F, each link includes an end surface 51 facing an adjacent link and, in some instances, end surfaces 51 of adjacent links are in contact when articulation joint 50 is in the straight configuration. For example, end surface 51 of first link 50a contacts an end surface 51 of an adjacent link 50a on one of four sides of articulation joint 50 (e.g., second side 58b) when articulation joint 50 is in the straight configuration (contact may include point contact between adjacent end surfaces 51 at second side 58b of adjacent links 50a, and/or contact between adjacent surfaces 51 of adjacent links 50a from second side 58b toward one or both of first and third sides 58a, 58c in a circumferential direction of articulation joint 50). For ease of understanding, only some end surfaces 51 are identified by a reference numeral in FIGS. 4A-4F. However, it will be understood that end surfaces 51 are provided at each end of every link.

On first side 58a of first link section 52, end surface 51 of one link 50a is spaced from end surface 51 of an adjacent link 50a, approaches end surface 51 of the adjacent link 50a as articulation joint 50 bends toward first side 58a, and contacts end surface 51 of the adjacent link 50a when articulation joint 50 is completely bent toward first side 58a, as shown in FIG. 4A. As described above, springs 24 connect adjacent links 50a on only two sides, e.g., third side 58c and fourth side 58d. In addition, springs 24 are tightly wound coiled springs with no spaces between adjacent coils when the spring is in a straight configuration. For this reason, links having a first link type 50a in first link section 52 are incapable of bending toward third side 58c or fourth side 58d. According to an embodiment, therefore links 50a of first link section 52 bend in a single direction, e.g., toward first side 58a.

As further shown in FIGS. 4B and 4E, end surface 51 of a second link 50b contacts end surface 51 of an adjacent link 50b on only one side, i.e., second side 58b, when articulation joint 50 is in the straight configuration. End surface 51 of third link type 50c does not contact end surface 51 of an adjacent link 50c when articulation joint 50 is in the straight configuration. When a second link 50b is bent toward first side 58a, end surface 51 of the second link 50b contacts end surface 51 of an adjacent second link 50b. When a third link 50c is bent toward first or second sides 58a, 58b, end surface 51 of the third link 50c contacts end surface 51 of an adjacent third link 50c. Contact between end surfaces 51 of adjacent links prevents further bending of adjacent links of articulation joint 50, and results in the maximum bend of articulation joint 50 in that specific direction.

Further, as shown in FIGS. 4A-4F, springs 24 are attached to all four sides 58a, 58b, 58c, 58d of second link section 54 and third link section 56. The springs 24 are attached to adjacent links at offset positions, however. For example, three adjacent links 100 (see FIG. 3) include two pairs of adjacent links. The first pair of adjacent links 100A, 100B is attached together by springs 24 on first and second sides 58a, 58b, such that the first pair of adjacent links 100A, 100B are unable to be bent relative to each other toward first and second sides 58a, 58b. The second pair of adjacent links 100B, 100C is attached together via springs 24 on third and fourth sides 58c, 58d. Second pair of adjacent links 100B, 100C are therefore unable to bend toward third and fourth sides 58c, 58d with respect to each other due to the arrangement of springs 24.

Adjacent links in each of first, second, and third link sections 52, 54, 56 are capable of bending with respect to each other in at least one direction. The angle at which adjacent links may bend and the spacing between these adjacent links may be equal to a smallest bend radius at which imaging wires and other components are capable of bending and remaining functional. For example, a largest bend angle B of adjacent links spaced apart by 0.3 inches to 0.7 inches is approximately 20 degrees to 40 degrees, preferably approximately 25 degrees to 35 degrees at a 0.4 inch to 0.6 inch spacing between adjacent links, and more preferably approximately 30 degrees at a 0.5 inch spacing between adjacent links.

Referring to FIGS. 4A-4C, longitudinal axis A extends in the Y-axis, and articulation joint 50 bends in the Y-Z plane. As shown in FIG. 4B, a first gap G is provided between adjacent links within the first link section 52, and between a distalmost link in first link section 52 and a proximalmost link of second link section 54, along a first side 58a of articulation joint 50. A second gap H is provided between adjacent links in second link section 54 on first side 58a. A third gap I is provided between links in third link section 56, and between a distalmost link of third link section 56 and distalmost link 29, on both first side 58a and second side 58b.

The first, second, and third gaps G, H, I allow articulation joint 50 to bend an amount equal to bend angle B multiplied by the number of total gaps. For example, if bend angle B is 30 degrees and there are seven total gaps on first side 58a, articulation joint 50 may bend 210 degrees from longitudinal axis A and allow tip 30 to point toward an entry point of endoscope 10 into the patient. The size of gaps G, H, and I may be varied to achieve a desired bend angle. It will also be understood that the bend angles are merely examples, and the bend angle of each different gap may be different for a gap type, e.g., each different gap G from the plurality of gaps G may have a different bend angle.

According to an example, third gaps I on second side 58b allow adjacent links to bend at a same angle B as first gaps G. However, that angle associated with third gaps I on second side 58b is not limited to angle B and may be any angle that optimizes the bend angle of articulation joint 50.

As shown in FIG. 4C, third gaps I allow third link section 56 and distalmost link 29 to bend away from longitudinal axis A toward second side 58b while first link section 52 and second link section 54 do not bend toward second side 58b, i.e., first link section 52 and second link section 54 remain coaxial with longitudinal axis A. This configuration allows articulation joint 50 to bend 90 degrees toward second side 58b. Since this bend is performed by bending at only some gaps, i.e., using only the three third gaps I, a bend radius of articulation joint 50 is reduced, thereby allowing articulation joint 50 to bend in smaller spaces. It will be understood that while second link section 54 is shown as being capable of bending in three directions, second link section 54 may be capable of bending in only two directions in some examples.

Figure 4D:
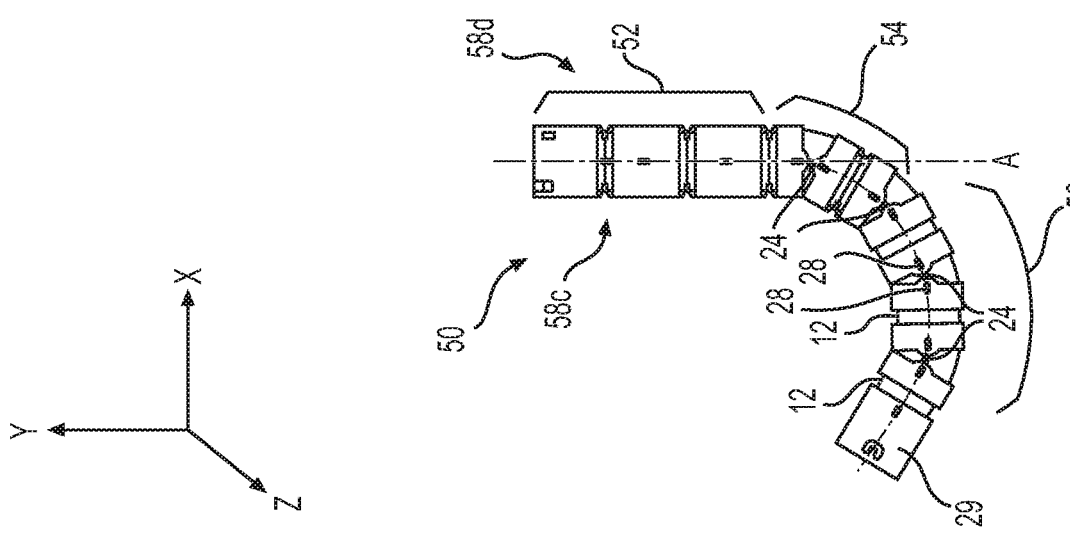

Referring to FIGS. 4D-4F, longitudinal axis A extends in the Y-axis and articulation joint 50 bends in the X-Y plane. As shown in FIG. 4E, second link section 54 and third link section 56 include a plurality of fourth gaps J on a third side 58c and a fourth side 58d of articulation joint 50, opposite third side 58c. Fourth gap J is also between the distalmost link of second link section 54 and the proximal most link of third link section 56, and the distalmost link of third link section 56 and distalmost link 29. Fourth gaps J are not present in first link section 52. According to an example, fourth gaps J permit adjacent links to bend at a same angle B as the angles associated with first, second, and third gaps G, H, I. However, the angle associated with fourth gaps J is not limited to angle B and may be any angle that optimizes the bend angle of articulation joint 50. As further shown by comparing FIG. 4B to FIG. 4E, fourth gaps J are offset, or alternate, along longitudinal axis A from first, second, and third gaps G, H, I. For example, as discussed above, adjacent links may bend with respect to each other in first and/or second directions 58a, 58b, but not in third and fourth directions 58c, 58d, based on the arrangement of springs 24. Similarly, adjacent links may bend with respect to each other in third and/or fourth directions 58c, 58d, but not in first and second directions 58a, 58b. Thus, in some examples, when a portion of articulation joint 50 is bent, two adjacent links may be bent together (e.g., first pair of adjacent links 100A, 100B may bend relative to each other toward one side or another).

Articulation joint 50 may bend in the X-Y plane with respect to longitudinal axis A. For example, if bend angle B is 30 degrees and there are four gaps J on each of third side 58c and fourth side 58d, articulation joint 50 may bend 120 degrees with respect to first link section 52 in both a left and right direction, i.e., toward third side 58c and fourth side 58d (i.e., a 120 degree deviation of second and third link sections 54, 56 from longitudinal axis A). This configuration again limits the number of gaps necessary to achieve a desired bend angle of articulation joint 50, thereby reducing the bend radius of articulation joint 50 to allow for greater maneuverability in smaller spaces. It will be understood that as articulation joint 50 bends toward one or more sides, surfaces defining the gaps at those side approach until the surfaces are in contact with each other and the respective gaps therefore completely close. A size of gaps on an opposite side of the bend will increase. Similarly, when articulation joint 50 moves from a bent position back toward the straight configuration, the closed gaps reopen, and the size of gaps on the opposite side of the bend will decrease. It will be understood that the angle of gap J on third side 58c and the angle of gap J on fourth side 58d do not need to be equal to each other and/or do not need to achieve the same total deviation of articulation joint 50 from longitudinal axis A. For example, gaps may be arranged on third side 58c and fourth side 58d such that a number of gaps and/or an angle of bend of the gaps on third side 58c is different than a number of gaps and/or an angle of bend of the gaps on fourth side 58d, resulting in different bend geometry at full flexion of articulation joint 50.

It will be apparent to those skilled in the art that various modifications and variations can be made to the disclosed device without departing from the scope of the disclosure. For examples, the configuration of gaps and links and the bend angles may be altered to suit any medical device. It will be understood that the bend angles, sizes of each gap, and/or the number of gaps and links are not limited to the examples described herein. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An articulation joint for a medical device, the articulation joint including:
   proximal links, distal links, and intermediate links connecting the proximal and distal links, wherein the articulation joint has a straight configuration along a straight longitudinal axis, a first bent configuration when the articulation joint bends toward a first side of the longitudinal axis, and a second bent configuration when the articulation joint bends toward a second side of the longitudinal axis, opposite to the first side,
   wherein, when the articulation joint is in the straight configuration:
      a first gap is defined at the first side between adjacent proximal links, and the adjacent proximal links contact each other at the second side,
      a second gap is defined at each of the first side and the second side between adjacent distal links, and
      a third gap is defined at the first side between adjacent intermediate links, and adjacent intermediate links contact each other at the second side.

2. The articulation joint according to claim 1, wherein when the articulation joint is in the first bent configuration, a size of each of the first, second, and third gaps on the first side, is smaller than a size of the first, second, and third gaps on the first side respectively when the articulation joint is in the straight configuration.

3. The articulation joint according to claim 1, wherein when the articulation joint is completely bent toward the first side, surfaces of adjacent links contact each other such that a size of each of the first, second, and third gaps on the first side is zero.

4. The articulation joint according to claim 1, wherein when the articulation joint is in the second bent configuration, a size of the second gaps on the second side is smaller than a size of the second gaps on the second side when the articulation joint is in the straight configuration.

5. The articulation joint according to claim 4, wherein the distal links are movable in exactly four directions, the proximal links are movable in exactly one direction, and the intermediate links are movable in two or three directions.

6. The articulation joint according to claim 1, wherein the articulation joint further includes a third bent configuration toward a third side of the longitudinal axis, intermediate to the first and second sides, and a fourth bent configuration when the articulation joint bends toward a fourth side of the longitudinal axis, opposite to the third side,
   wherein when the articulation joint is in the straight configuration:

a fourth gap is defined at each of the third side and the fourth side between the adjacent distal links; and a fifth gap is defined at each of the third side and the fourth side between the adjacent intermediate links.

7. The articulation joint according to claim 6, wherein when the articulation joint is in the third bent configuration, a size of each of the fourth gaps and the fifth gaps on the third side is smaller than a size of the fourth gaps and the fifth gaps on the third side respectively when the articulation joint is in the straight configuration, and wherein when the articulation joint is in the fourth bent configuration, a size of each of the fourth gaps and the fifth gaps on the fourth side is smaller than a size of the fourth gaps and the fifth gaps on the fourth side respectively when the articulation joint is in the straight configuration.

8. The articulation joint according to claim 6, wherein the fourth gaps and the fifth gaps are offset from the first, second, and third gaps along the longitudinal axis.

9. The articulation joint according to claim 6, wherein the articulation joint is configured to bend toward one of the first or the second side and one of the third or the fourth side at a same time.

10. The articulation joint according to claim 6, wherein a bend angle associated with each of the first, second, third, fourth, and fifth gaps is equal.

11. The articulation joint according to claim 1, wherein the proximal links, distal links, and intermediate links of the articulation joint are each attached to an adjacent link by a first spring and a second spring, and wherein the first spring and the second spring of attached links are on circumferentially opposite sides of the articulation joint.

12. The articulation joint according to claim 11, wherein the first and the second springs are attached on an inner surface of each of the proximal links, distal links, and intermediate links by one or more of laser welding or an adhesive.

13. The articulation joint according to claim 11, wherein adjacent coils of each of the first spring and the second spring contact each other when the first springs and the second springs are in a straight configuration.

14. The articulation joint according to claim 11, wherein each of the first spring and the second spring defines a lumen for containing an articulation element.

15. An articulation joint for an endoscope, the articulation joint comprising:
proximal links, distal links, and intermediate links connecting the proximal and distal links, wherein the articulation joint has a straight configuration along a straight longitudinal axis,
wherein the proximal links are movable toward only a first side of the articulation joint away from the longitudinal axis,
wherein the distal links are movable toward the first side, a second side, a third side, and a fourth side of the articulation joint away from the longitudinal axis, wherein the first, second, third, and fourth sides are equally spaced about the longitudinal axis, and
wherein the intermediate links are movable only toward the first side, the second side, and the third side of the articulation joint away from the longitudinal axis.

16. The articulation joint according to claim 15, further comprising, in the straight configuration, gaps between links of the proximal links, the distal links, and the intermediate links at locations where the articulation joint bends, wherein when the articulation joint completely bends toward each of the first, second, third, and fourth sides, surfaces of adjacent links contact each other along the respective side, and a size of the gaps along the respective side is zero.

17. An endoscope, comprising:
a handle; and
a catheter connected to the handle and extending distally, the catheter comprising:
a shaft extending distally from the handle;
a tip member provided at a distalmost end of the catheter; and
an articulation joint connecting the tip member to the shaft,
wherein the articulation joint includes a proximal portion, a distal portion, and an intermediate portion arranged about a longitudinal axis,
the proximal portion is bendable in only a first direction away from the longitudinal axis,
the intermediate portion is bendable in the first direction, a second direction, a third direction, and a fourth direction away from the longitudinal axis, and
the distal portion is bendable in only the first, second, and third directions.

18. The endoscope according to claim 17, wherein the distal portion, the intermediate portion, and the proximal portion of the articulation joint include a plurality of adjacent links each connected by two springs on radially opposite sides of the articulation joint.

19. The articulation joint according to claim 1, wherein:
when the articulation joint is in the first bent configuration, the articulation joint bends, at a first bend radius, to a first bend angle that is a maximum bend angle,
when the articulation joint is in the second bent configuration, the articulation joint bends, at a second bend radius, to a second bend angle that is smaller than the first bend angle, and
the first bend radius is the same as the second bend radius.

20. The articulation joint according to claim 11, wherein:
the first and second springs attaching a first pair of adjacent links, including a first link and a second link, are respectively on a first side of the articulation joint and a second side of the articulation opposite the first side, and
the first and second springs attaching a second pair of adjacent links, including the second link and a third link, are respectively on a third side of the articulation joint, intermediate to the first and second sides, and a fourth side opposite the third side of the articulation joint.

* * * * *